United States Patent [19]

Tokunaga et al.

[11] Patent Number: 5,068,365

[45] Date of Patent: Nov. 26, 1991

[54] HEXAHYDROPHTHALIC ANILIDE DERIVATIVES

[75] Inventors: Takumi Tokunaga; Hiroyuki Watanabe; Kenji Tsuzuki, all of Yamaguchi; Sinzo Someya, Saitama; Seigo Koura, Tokyo; Mikio Ito, Yamaguchi, all of Japan

[73] Assignees: Tosoh Corporation, Yamaguchi; Agro-Kanesho Co., Ltd., Tokyo, both of Japan

[21] Appl. No.: 292,077

[22] Filed: Dec. 30, 1988

[30] Foreign Application Priority Data

Dec. 31, 1987 [JP] Japan .................. 62-336452
Sep. 7, 1988 [JP] Japan .................. 62-222256
Sep. 8, 1988 [JP] Japan .................. 63-225462
Sep. 19, 1988 [JP] Japan .................. 63-234259

[51] Int. Cl.$^5$ .................. C07C 69/75; C07D 307/16
[52] U.S. Cl. .................. 549/496; 548/127; 548/128; 548/133; 548/194; 548/233; 548/301; 548/315; 548/358; 548/362; 549/420; 558/414; 560/45; 564/89; 564/91
[58] Field of Search .................. 548/127, 128, 133, 194, 548/233, 301, 315, 358, 362; 549/420, 496; 558/414; 560/45; 564/89, 91

[56] References Cited

U.S. PATENT DOCUMENTS 2,821,467 1/1958 Lewis .................. 71/2.6
4,003,926 1/1977 Goddard .................. 260/518

FOREIGN PATENT DOCUMENTS 0097056 12/1983 European Pat. Off. .
2457853 12/1980 France .
59-67255 6/1984 Japan .
2023137 12/1979 United Kingdom .

OTHER PUBLICATIONS

*Agr. Biol. Chem.*, 40(4), 745-751, 1976, Ohta et al, "Structure-Activity Relationship of Cyclic Imide Herbicides".
Chemical Abstracts, vol. 105, No. 11, 15th Sep. 1986, p. 605, Abstract No. 97171d . . . (Toyo Soda Mfg. Co., Ltd), 17-02-86.

Primary Examiner—Richard L. Raymond
Attorney, Agent, or Firm—Nixon & Vanderhye

[57] ABSTRACT

Disclosed is novel hexahydrophthalic anilide derivatives and herbicide compositions comprising the derivatives. The hexahydrophthalic anilide derivatives of this invention are represented by the formula [I], [II] or [III].

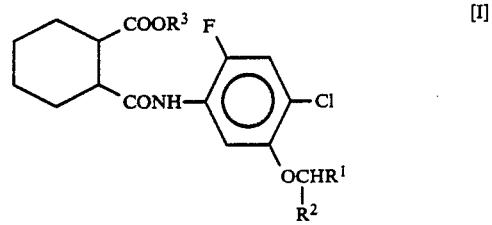

(wherein $R^1$ represents non-substituted or substituted phenyl, $R^2$ represents hydrogen or $C_1$-$C_4$ alkyl, $R^3$ represents $C_1$-$C_4$ alkyl or $C_1$-$C_4$ alkenyl)

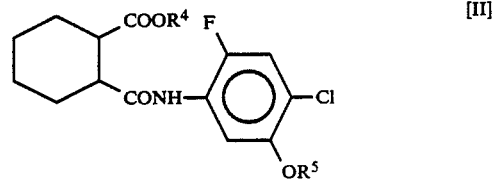

(wherein $R^4$ and $R^5$, the same or different, represent $C_1$-$C_4$ alkyl, $C_1$-$C_4$ alkenyl or $C_1$-$C_4$ alkynyl, provided $R^4$ and $R^5$ are not $C_1$-$C_4$ alkyl simultaneously)

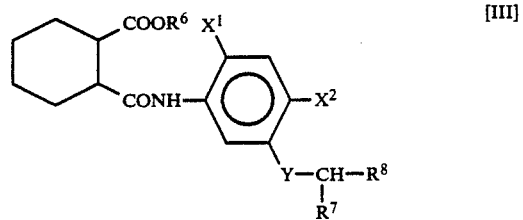

(wherein $X^1$ and $X^2$, the same or different, represent halogen, Y represents oxygen or sulfur, $R^6$ represents $C_1$-$C_6$ straight or cyclic alkyl which may be substituted with oxygen, $R^7$ represents hydrogen or methyl, $R^8$ represents cyano, $C_1$-$C_3$ alkyl, $C_2$ or $C_3$ alkenyl, $C_2$-$C_4$ alkynyl, $C_3$-$C_6$ alkynyl which is substituted with methoxy, $CONHR^9$ (wherein $R^9$ represents aromatic sulfonyl) or azole heterocyclic ring)

8 Claims, No Drawings

HEXAHYDROPHTHALIC ANILIDE DERIVATIVES

BACKGROUND OF THE INVENTION

I. Field of the Invention

This invention relates to novel hexahydropthalic acid anilide derivatives which have high herbicidal activity and selectivity.

II. Description of the Related Art

The herbicidal activity of hexahydrophthalic anilide derivatives is well-known in the art. For example, Japanese Patent Disclosure (Kokai) No. 33154/86 discloses N-(4-chloro-2-fluoro-5-isopropoxyphenyl)-2-ethoxycarbonylcyclohexylcarboxylic amide.

However, some of the known hexahydrophthalic anilide derivatives do not have satisfactory herbicidal activity. The other known hexahydrophthalic anilide derivatives do not have satisfactory selectivity. That is, when the herbicide comprising the derivative is applied to the crops and weeds, not only the weeds, but also the crops may be damaged. Thus, the safety of the herbicide is not good.

SUMMARY OF THE INVENTION

Accordingly, the object of the present invention is to provide novel hexahydrophthalic anilide derivatives which have a high herbicidal activity and selectivity.

Another object of the present invention is to provide herbicide compositions having a high herbicidal activity and selectivity.

The present inventors intensively studied to find that specific hexahydrophthalic anilide derivatives have a high herbicidal activity and selectivity to complete the present invention.

That is, the present invention provides novel hexahydrophthalic anilide derivatives which are represented by one of the following formulae [I]–[III]:

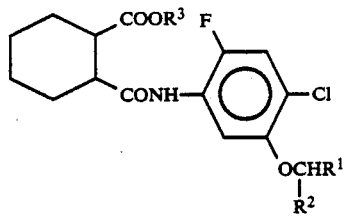

(wherein $R^1$ represents non-substituted or substituted phenyl, $R^2$ represents hydrogen or $C_1$–$C_5$ alkyl, $R^3$ represents $C_1$–$C_5$ alkyl or $C_1$–$C_5$ alkenyl)

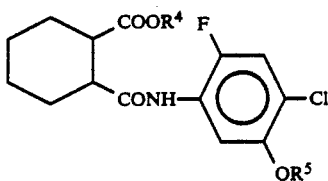

(wherein $R^4$ and $R^5$, the same or different, represent $C_1$–$C_6$ alkyl, $C_1$–$C_6$ alkenyl or $C_1$–$C_6$ alkynyl, provided $R^4$ and $R^5$ are not $C_1$–$C_6$ alkyl simultaneously)

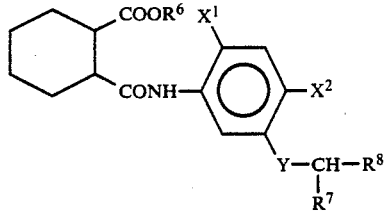

(wherein $X^1$ and $X^2$, the same or different, represent halogen, Y represents oxygen or sulfur, $R^6$ represents $C_1$–$C_6$ straight or cyclic alkyl which may be substituted with oxygen, $R^7$ represents hydrogen or methyl, $R^8$ represents cyano, $C_1$–$C_3$ alkyl, $C_2$ or $C_3$ alkenyl, $C_2$–$C_4$ alkynyl, $C_3$–$C_6$ alkynyl which is substituted with methoxy, $CONHR^9$ (wherein $R^9$ represents aromatic sulfonyl) or azole heterocyclic ring)

By the present invention, novel hexahydrophthalic anilide derivatives with high herbicidal activity and selectivity was provided. As will be clearly demonstrated in the Examples later described, the hexahydrophthalic anilide derivatives of the present invention have a high herbicidal activity while they do not substantially damage the useful crops such as wheat, corn and soybean. Thus, they can be used safely for the inhibition of the growth of weeds in the field of such crops.

DETAILED DESCRIPTION OF THE PREFERRED EMBODIMENTS

In one aspect, the present invention provides the hexahydrophthalic anilide derivative represented by the above-described formula [I]. In formula [I], $R^1$ is non-substituted or substituted phenyl, $R^2$ is hydrogen or $C_1$–$C_5$ alkyl and $R^3$ is $C_1$–$C_5$ alkyl or $C_1$–$C_5$ alkenyl. Preferred examples of $R^1$ may include toluyl, xylyl, ethylphenyl, propylphenyl, butylphenyl and phenyl. The most preferred $R^1$ is phenyl. Preferred examples of $R^2$ may include hydrogen and straight or branched $C_1$–$C_5$ alkyl such as methyl, ethyl and propyl. Among these, the most preferred are hydrogen and methyl. Preferred examples of $R^3$ may include straight or branched $C_1$–$C_5$ alkyl such as methyl, ethyl and propyl, and $C_3$ or $C_4$ alkenyl such as allyl and butenyl. Among these, the most preferred are ethyl and allyl.

Preferred and non-limiting specific examples of the hexahydrophthalic anilide derivatives represented by the formula [I] are summarized in Table 1 below.

TABLE 1

| Compound No. | $R^1$ | $R^2$ | $R^3$ |
| --- | --- | --- | --- |
| 1 | phenyl | H | $C_2H_5$ |
| 2 | phenyl | $CH_3$ | $C_2H_5$ |
| 3 | phenyl | $CH_3$ | allyl |

In another aspect, the present invention provides the novel hexahydrophthalic anilide derivative represented by the above-described formula [II]. In the formula [II], $R^4$ and $R^5$, the same or different, represent $C_1$–$C_6$ alkyl, $C_1$–$C_6$ alkenyl or $C_1$–$C_6$ alkynyl. However, $R^4$ and $R^5$ are not $C_1$–$C_6$ alkyl simultaneously. Preferred examples of $R^4$ and $R^5$ may include $C_1$–$C_6$, preferably $C_1$–$C_5$ straight and branched alkyl such as methyl, ethyl, n-propyl and isopropyl; $C_3$ and $C_4$ alkenyl such as allyl, 2-methyl-2-propenyl and 2-butenyl; and $C_3$ and $C_4$ alkynyl such as propargyl, 1-methyl-2-propynyl and 2-butynyl.

Preferred and non-limiting specific examples of the hexahydrophthalic anilide derivative of formula [II] are listed in Table 2 below.

TABLE 2

| Compound No. | $R^4$ | $R^5$ |
|---|---|---|
| 4 | $C_2H_5$ | $CH_2CH=CH_2$ |
| 5 | $C_2H_5$ | $CH_2C\equiv CH$ |
| 6 | $CH_2CH=CH_2$ | $CH(CH_3)_2$ |
| 7 | $CH_2C\equiv CH$ | $CH(CH_3)_2$ |
| 8 | $CH_2CH=CH_2$ | $CH_2CH=CH_2$ |
| 9 | $CH_2CH=CH_2$ | $CH_2C\equiv CH$ |
| 10 | $CH_2C\equiv CH$ | $CH_2CH=CH_2$ |
| 11 | $CH_2C\equiv CH$ | $CH_2C\equiv CH$ |
| 12 | $CH_2CH=CH_2$ | $CH(CH_3)C\equiv CH$ |
| 13 | $CH_2C\equiv CH$ | $CH(CH_3)CH=CH_2$ |

In still another aspect, the present invention provides the novel hexahydrophthalic anilide derivative represented by the above-described formula [III]. In formula [III], $X^1$ and $X^2$ represent halogen and they may be the same or different. Preferred examples of $X^1$ and $X^2$ include fluorine and chlorine. Y represents oxygen or sulfur. $R^6$ represents straight or cyclic $C_1$-$C_6$ alkyl which may be substituted with oxygen. Preferred examples of $R^6$ may include alkoxylalkyl such as methoxyethyl, ethoxyethyl, methoxypropyl and ethoxypropyl; and alkyl which is substituted with a heterocyclic ring containing oxygen such as 2-tetrahydrofuranylmethyl and 2-perhydropyranylmethyl. Among these, the most preferred are methoxyethyl and 2-tetrahydrofuranylmethyl. $R^7$ represents hydrogen or methyl. $R^8$ represents cyano, $C_1$-$C_3$ alkyl, $C_2$ or $C_3$ alkenyl, $C_2$-$C_4$ alkynyl, $C_3$-$C_6$ alkynyl substituted with methoxy, $CONHR^9$ ($R^9$ is aromatic sulfonyl) or azole heterocyclic ring such as oxazolyl, imidazolyl, pyrazolyl, thiazolyl, oxadiazolyl and thiadiazolyl. Preferred examples of $R^8$ may include cyano; $C_1$-$C_3$ alkyl such as methyl, ethyl, propyl and isopropyl; alkenyl such as vinyl, propenyl and butenyl; alkynyl such as ethynyl, propynyl and butynyl; alkynyl substituted with methoxy such as 3-methoxypropynyl, 4-mehtoxybutynyl and 5-methoxypentynyl; secondary amide of which nitrogen atom is substituted with sulfonyl such as methylphenylsulfonyl, chlorophenylsulfonyl and anisylsulfonyl; azole heterocyclic ring such as 5-(1,2,4-oxadiazolyl) of which 3-position is substituted with $C_1$-$C_3$ alkyl such as methyl, ethyl and propyl.

Preferred and non-limiting specific examples of the hexahydrophthalic anilide derivative represented by the formula [III] are listed in Table 3 below.

TABLE 3

| Compound No. | $X^1$ | $X^2$ | Y | $R^6$ | $R^7$ | $R^8$ |
|---|---|---|---|---|---|---|
| 14 | F | Cl | O | $CH_2CH_2OMe$ | Me | Me |
| 15 | F | Cl | S | $CH_2CH_2OMe$ | H | $CH=CH_2$ |
| 16 | F | Cl | O | $CH_2CH_2OMe$ | H | $C\equiv CH$ |
| 17 | F | Cl | O | $CH_2CH_2OMe$ | Me | $C\equiv CH$ |
| 18 | F | Cl | O | $CH_2CH_2OMe$ | Me | $CH_2C\equiv CH$ |
| 19 | F | Cl | O | $CH_2CH_2OMe$ | H | $C\equiv CCH_2OMe$ |
| 20 | F | Cl | S | $CH_2CH_2OMe$ | H | $C\equiv CH$ |
| 21 | Cl | Cl | O | $CH_2CH_2OMe$ | Me | $C\equiv CH$ |
| 22 | F | Cl | O | (tetrahydrofuranyl-CH$_2$-) | Me | $C\equiv CH$ |
| 23 | F | Cl | O | $CH_2CH_2OMe$ | Me | $C\equiv N$ |
| 24 | F | Cl | O | $CH_2CH_2OMe$ | Me | (3-methyl-1,2,4-oxadiazol-5-yl) |
| 25 | F | Cl | O | $CH_2CH_2OMe$ | Me | $CONHSO_2$-C$_6$H$_4$-OMe |

Me: $CH_3$

The hexahydrophthalic anilide derivative represented by the formula [I] may be prepared by reacting the aniline derivative represented by formula [IV] and the acid halide represented by formula [V] according to the following Equation 1:

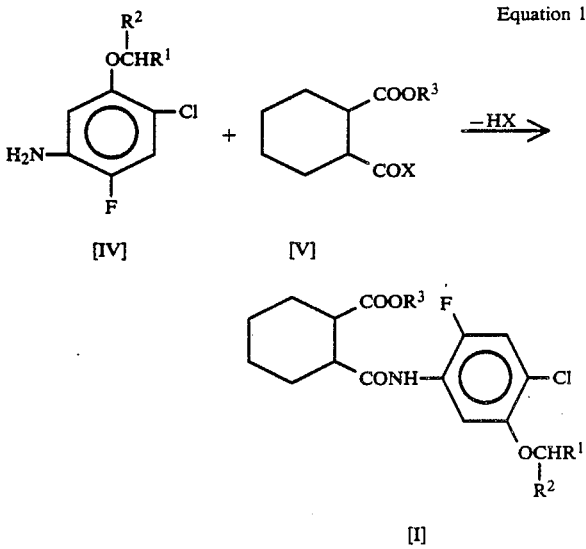

Equation 1

In the above Equation 1, X means halogen, preferably chlorine, bromine and iodine. $R^1$, $R^2$ and $R^3$ represent the same meaning as in formula [I].

The reaction may be conducted in an appropriate solvent under the presence of a base at a temperature ranging from 0° C.-150° C., preferably 20° C.-100° C. for several minutes to 48 hours.

Preferred examples of the solvents which may be employed in the reaction may include ketones such as acetone and methyl ethyl ketone; aromatic hydrocarbons such as benzene and xylene; ethers such as ethyl ether, tetrahydrofuran and dioxane; halogenated hydrocarbons such as chlorobenzene, chloroform, tetrachloromethane and dichloroethane; tertiary amines such as triethylamine, pyridine and dimethylaniline; and polar solvents such as acetonitrile, dimethylformamide, dimethylsulfoxide and hexamethylphosphoramide.

Preferred examples of the bases which may be employed in the reaction may include amines such as triethylamine, pyridine, 1,3-diazabicyclo[5,4,0]undec-7-ene and dimethylaniline; alkali metal hydroxide such as sodium hydroxide; alkaline earth metal hydroxides such as calcium hydroxide; alkaline metal salts of carbonic acid such as sodium carbonate, potassium carbonate, sodium hydrogen carbonate and potassium hydrogen carbonate; and metal hydrides such as sodium hydride.

Typically, 1-5 equivalents of the aniline derivative [IV] and 1-10 equivalents of the base are reacted with 1 equivalent of the acid halide [V].

The hexahydrophthalic anilide derivative represented by formula [II] may be prepared by reacting the aniline derivative represented by formula [VI] and the acid halide represented by formula [VII] according to the following Equation 2:

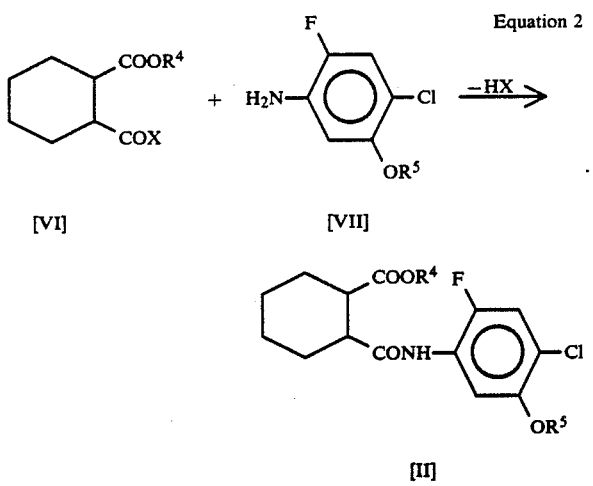

In the above Equation 2, X represents the same meaning as in Equation 1, $R^4$ and $R^5$ represent the same meaning as in formula [II].

The reaction may be conducted in the same conditions as in Equation 1. The solvents and bases which are preferred in Equation 1 are also preferred in this reaction.

Typically, 1-5 equivalents of the aniline derivative [VII] and 1-10 equivalents of the base are reacted with 1 equivalent of the acid halide [VI].

The hexahydrophthalic anilide derivative represented by formula [III] may be prepared by reacting the aniline derivative represented by formula [IX] and the acid halide represented by formula [VIII] according to the following Equation 3:

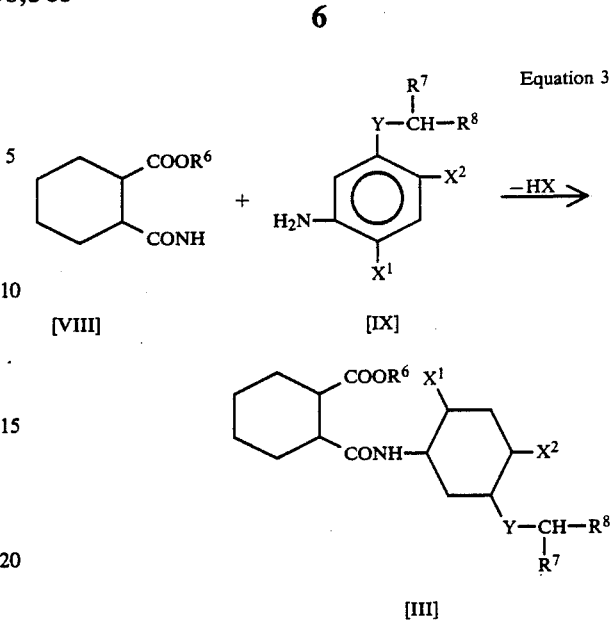

In the above Equation 3, X represents the same meaning as in Equation 1, $X^1$, $X^2$, $R^6$, $R^7$ and $R^8$ represent the same meaning as in formula [III].

The reaction may be conducted in the same conditions as in Equation 1. The solvents and bases which are preferred in Equation 1 are also preferred in these reactions.

Typically, 1-5 equivalents of the aniline derivative [IX] and 1-10 equivalents of the base are reacted with 1 equivalent of the acid halide [VIII].

The present invention further provides a herbicide composition comprising the hexahydrophthalic anilide derivative of the present invention as effective ingredient in an agriculturally acceptable carrier. The herbicide composition of the present invention is effective for inhibiting the growth of various weeds growing in paddy field including the weeds belonging to the Gamineae such as barnyardgrass; broadleaved weeds such as Falsepinpernel, spindle-flowered rotala, water starwart and monochoria; and those belonging to the family cyperaceae such as small flower umbrellaplant, slender spikerush and water nutgrass. Further, the hexahydrophthalic anilide derivative of the present invention is particularly effective for inhibiting the growth of weeds growing in fields, such as mustard, virginia pepperweed, catchweed badstraw, Kinutaso (Galium kinuta), chick weed, Common lambsquaters, nottle (Utrica Thunbergiana), Common groundsel, Slender amaranth, Cocklebur, Pale smartweed, Velvetleaf and barynard grass. The herbicide composition of the present invention does not substantially damage the crops belonging to Family Graminae such as corn, rice and wheat, so that it is highly safe.

The agriculturally acceptable carriers per se which may be employed in the present invention are well-known in the art, and either liquid carrier or solid carrier may be employed. Preferred examples of the liquid carrier or diluent may include water, hydrocarbons, ethers, alkoxy alcohols, ketones, esters, amides and sulfoxides. Preferred examples of the solid carriers or extender may include powder and granules of inorganic materials such as slaked lime, gypsum, calcium carbonate, silica, pearlite, pumice, diatomaceous earth, alumina, zeolite and clay minerals (e.g., talc, vermiculite and kaolinite); powder and granules of plant products such as starch, cereals and glucose; and powder and granules of synthetic products such as phenol resins, carbon resins and vinyl chloride resins. The concentration of the active ingredient in the composition is not critical and may usually be 0.1% by weight to 90% by weight, preferably 1% by weight to 80% by weight.

If necessary, the herbicide composition of the present invention may contain a surfactant. The surfactants are well-known and widely used in the art. Preferred examples of the surfactants include anion surfactants such as alkylsulfate esters, arylsulfonic acids, salts of succinic acid and polyethyleneglycolalkylaryl ethers and ester salts of sulfuric acid; cation surfactants such as alkylamines and polyoxyethylenealkylamines; non-ionic surfactants such as polyoxyethyleneglycol ethers and polyol esters; and ampholytic surfactants. If desired, the herbicide composition of the present invention may contain other additives which are often employed in herbicide compositions. The examples of such additives may include stabilizers, dispersion stabilizers, fixing agents, effect prolongers and synergists. The herbicide composition of the present invention may also contain other herbicides, bacteriocides, fungicides and the like.

The herbicide composition may be formulated to an emulsifiable concentrate, wettable powder, aqueous solution, oily solution, granule or powder. The methods of formulating herbicide composition are well-known in the art.

Specific non-limiting examples of the preferred compositions of the present invention will now be described. In the following examples, all parts are based on weight.

FORMULATION 1

Emulsifiable Concentrate

| | |
|---|---|
| Compound of the present invetnion: | 20 parts |
| xylene: | 60 parts |
| Solpol (a surfactant commercially available from Toho Kogaku Kogyo) | 20 parts |

This formulation may be prepared by uniformly mixing the components.

FORMULATION 2

Wettable Powder

| | |
|---|---|
| Compound of the present invetnion | 10 parts |
| Zeaklite | 87 parts |
| Neoplex Powder (commercially available rom Kao corporation) | 1.5 parts |
| Solpol (a surfactant commercially available from Toho Kogaku Kogyo) | 1.5 parts |

This composition may be prepared by mixing and pulverizing the components.

The amount of the compound of the present invention to be applied to the field varies depending on the formulation of the composition, method of application, species and stage of growth of the weeds. Typically, the amount to be applied may be 0.01 kg to 10 kg, preferably 0.05 kg to 5 kg per hectare in terms of the weight of the active ingredient of the present invention.

The herbicide composition of the present invention may directly be applied to the leaves or stems of weeds or to the field before the germination of the weeds The herbicide composition may be applied as it is or may be diluted with water before use.

The invention will now be described by way of the examples thereof. It should be understood that the examples are presented for the illustration purpose only and should not be interpreted any restrictive way.

EXAMPLE 1

Preparation of N-(5-benzyloxy-4-chloro-2-fluorophenyl)2-ethoxycarbonyl cyclohexyl carboxylic amide (Compound No. 1 (Table 1))

In 20 ml of methylene chloride, 400 mg of 1,2,3,4,5,6-hexahydrophthalic acid monoethylester was dissolved. To this solution, 0.16 ml of pyridine and 0.16 ml of thionyl chloride were added and the mixture was stirred at room temperature. One hour later, 0.45 g of 5-benzyloxy-4-chloro-2-fluoroaniline and 10 ml of triethylamine were added and the resulting mixture was stirred at room temperature for 2.5 hours. After completion of the reaction, 10% hydrochloric acid was added to the reaction mixture to make the mixture acidic and the resulting mixture was extracted twice with methylene chloride. The extract was washed with saturated aqueous sodium hydrogen carbonate solution and was dried over anhydrous magnesium sulfate. The solvent was then evaporated and the residue was purified by column chromatography (silica gel, hexane/ethyl acetate =3/1 (v/v)) to obtain 0.35 g of solid.

m.p.: 78° C.-80° C.

| | Element Analysis | | |
|---|---|---|---|
| | C | H | N |
| Found (%) | 63.89 | 5.75 | 2.85 |
| Calcd. (%) | 63.66 | 5.80 | 3.22 |

IR (KBr, cm$^{-1}$): 3320, 1725, 1690

PMR (CDCl$_3$, δ ppm) 1.10–2.40 (m, 11H), 2.56–3.20 (m, 2H), 4.10 (q, J =7 Hz, 2H), 5.10 (s, 2H), 7.06 (d, J =10 Hz, 1H), 7.15–7.55 (m, 5H), 7.70 (brs, 1H), 8.16 (d, J =7 Hz, 1H)

EXAMPLE 2

Preparation of Compound No. 2

Substantially the same operation as in Example 1 was repeated except that 4-chloro-2-fluoro-5-(1-phenylethyloxy)aniline was used as the aniline derivative to obtain the Compound No. 2.

m.p.: 108° C.-110° C.

| | Element Analysis | | |
|---|---|---|---|
| | C | H | N |
| Found (%) | 64.15 | 6.03 | 3.31 |
| Calcd. (%) | 64.35 | 6.07 | 3.12 |

IR (KBr, cm$^{-1}$): 3320, 1725, 1690

PMR (CDCl$_3$, δ ppm) 0.90–2.45 (m, 14H), 2.50–3.10 (m, 2H), 4.09 (q, J =7 Hz, 2H), 5.39 (q, J =6 Hz, 1H), 7.00 (d, J =10 Hz, 1H), 7.10–7.50 (m, 5H), 7.68 (brs, 1H), 8.03 (d, J =7 Hz, 1H)

EXAMPLE 3

Preparation of Compound No. 3

Substantially the same operation as in Example 1 was repeated except that 1,2,3,4,5,6-hexahydrophthalic acid monoallyl ester was used as the hexahydrophthalic acid monlalkyl ester and 4-chloro-2-fluoro5-(1-phenylethyloxy)aniline was used as the anilide derivative to obtain the Compound No. 3.

m.p.: 54° C.–56° C.

| Element Analysis | C | H | N |
|---|---|---|---|
| Found (%) | 65.21 | 5.87 | 3.14 |
| Calcd. (%) | 65.28 | 5.91 | 3.04 |

IR (KBr, cm$^{-1}$) 3320, 1725, 1690

PMR (CDCl$_3$, δ ppm) 1.00–2.50 (m, 11H), 2.50–3.15 (m, 2H), 4.52 (d, J =5 Hz, 2H), 4.90–6.22 (m, 4HO, 7.00 (d, J =10 Hz, 1H), 7.05–7.53 (m, 5H), 7.58 (brs, 1H), 8.03 (d, J =7 Hz, 1H)

EXAMPLE 4

Test for Evaluation of Effectiveness in Growth Inhibition by Soil Treatment

Paddy field soil was packed in a plastic pot with 60 cm diameter. After pudding, the seeds of weeds shown in Table 4 below were sown and one seedling of rice (variety: Yamahoshi) with 2 leaves were transplanted. The water level was kept at about 3 cm above the soil. The herbicide compositions formulated according to the above-described Formulation 2 which contained the Compound No. 1, 2 or 3 was diluted with water and was uniformly applied to the water surface in the amount shown in Table 4. Further, for comparison, N-(4-chloro-2-fluoro-5-isopropoxyphenyl)2-ethoxycarbonyl cyclohexyl.carboxylic amide (Comparative Compound A) disclosed in Japanese Patent Disclosure (Kokai) No. 33154/86 was also tested. After 20 days from the application of the herbicide, the growing conditions of the weeds and the rice were observed. The growth inhibition was rated in 6 ranks as follows: follows:

Rank 0: percent growth inhibition of 0%–9%
Rank 1: percent growth inhibition of 10%–29%
Rank 2: percent growth inhibition of 30%–49%
Rank 3: percent growth inhibition of 50%–69%
Rank 4: percent growth inhibition of 70%–89%
Rank 5: percent growth inhibition of 90%–100%

The results are shown in Table 4.

TABLE 4

| Compound No. | Rate (a.i. g/10a) | Rice | Barnyard-grass | Small flower umbrellaplant | Monochoria | Annual broadleaved weeds |
|---|---|---|---|---|---|---|
| 1 | 250 | 0 | 5 | 5 | 5 | 5 |
|  | 125 | 0 | 5 | 5 | 5 | 5 |
|  | 60 | 0 | 5 | 4 | 4 | 5 |
| 2 | 250 | 0 | 5 | 5 | 5 | 5 |
|  | 125 | 0 | 5 | 5 | 5 | 5 |
|  | 60 | 0 | 5 | 5 | 5 | 5 |
| 3 | 250 | 0 | 5 | 5 | 5 | 5 |
|  | 125 | 0 | 5 | 5 | 5 | 5 |
|  | 60 | 0 | 5 | 5 | 5 | 5 |
| Comparative Compound A | 250 | 4 | 5 | 5 | 5 | 5 |
|  | 125 | 4 | 5 | 5 | 5 | 5 |
|  | 60 | 3 | 5 | 5 | 5 | 5 |

EXAMPLE 5

Test for Evaluation of Effectiveness in Growth Inhibition by Foliage Treatment Field soil was packed in a plastic vat sizing 22 cm ×16 cm and seeds of wheat (*Triticum aestivum*), corn (*Zea mays*) and soybean (*Glycine max*) were sown. The field soil was covered with soil of about 1 cm thickness which contains seeds of weeds, i.e., Slender amaranth, Velvetleaf and Cocklebur. When the barnyardgrass grew to have 2–2.5 leaves, the Compound No. 3 of the present invention was applied in the amount shown in Table 5 below. Further, for comparison, the comparative compound A described in Example 4 was also applied. After 14 days from the application of the herbicide, the conditions of the growth of the weeds and the crops were observed. The results are shown in Table 5. The herbicidal effectiveness was rated in 6 ranks as in Example 4.

TABLE 5

| Compound No. | Rate (a.i. g/10a) | Soybean | Wheat | Corn | Slender amaranth | Velvetleaf | Cocklebur |
|---|---|---|---|---|---|---|---|
| 3 | 250 | 0 | 0 | 0 | 5 | 5 | 4 |
|  | 125 | 0 | 0 | 0 | 5 | 5 | 4 |
|  | 60 | 0 | 0 | 0 | 5 | 5 | 3 |
| Comparative Compound D | 250 | 4 | 0 | 0 | 5 | 5 | 5 |
|  | 125 | 4 | 0 | 0 | 5 | 5 | 5 |
|  | 60 | 3 | 0 | 0 | 5 | 5 | 5 |

EXAMPLE 6

Preparation of N-(5-allyloxy-4-chloro-2-fluorophenyl)-2-ethoxycarbonyl cyclohexyl carboxylic amide (Compound No. 4)

In 20 ml of methylene chloride, 1.20 g of 1,2,3,4,5,6-hexahydrophthalic acid monoethyl ester was dissolved. To this solution 0.47 g of pyridine and 0.71 g of thionyl chloride were added and the resulting mixture was stirred at room temperature. Two hour later, 1 20 g of 5-allyloxy-4-chloro-2-fluoroaniline and 0.61 g of triethylamine were added and the resulting mixture was stirred at room temperature for 5 hours. After completion of the reaction, 10% hydrochloric acid was added to the reaction mixture to make the same acidic and was extracted twice with methylene chloride. The extract was washed with saturated aqueous sodium hydrogen carbonate and dried over magnesium sulfate. The solvent was evaporated under reduced pressure and the residue was purified by column chromatography (silica gel, hexane/ethyl acetate =5/1 (v/v)) to obtain 1.5 g of light brown crystal.

m.p.: 52° C.-53° C.

$^1$H-NMR (CDCl$_3$, δ ppm) 1.17 (3H, t), 1.10-2.50 (8H, m), 2.50-3.07 (2H, m), 4.10 (2H, q), 4.56 (2H, d), 5.10-5.56 (2H, m), 5.63-6.50 (1H, m), 7.05 (1H, d, J =10 Hz), 7.67 (1H, br), 8.07 (1H, d, J =7 Hz)

EXAMPLE 7

Preparation of Compound No. 5 (Table 2)

Substantially the same operation as in Example 6 was repeated except that 4-chloro-2-fluoro-5-propargyloxyaniline was used as the aniline derivative to obtain the Compound No. 5.

m.p.: 76° C.-77° C.

$^1$H-NMR (CDCl$_3$, δ ppm) 1.13 (3H, t), 1.00-2.35 (8H, m), 2.50 (1H, t), 2.63-3.20 (2H, m), 4.08 (2H, q), 4.73 (2H, d), 7.10 (1H, d, J =10), 7.76 (1H, br), 8.20 (1H, d, J =7)

EXAMPLE 8

Preparation of Compound No. 6 (Table 2)

Substantially the same operation as in Example 6 was repeated except that 2-chlorocarbonyl-1-cyclohexane carboxylic acid allyl ester was used as the acid halide, and 4-chloro-2-fluoro-5-isopropoxyaniline was used as the aniline derivative to obtain the Compound No. 6.

Refractive Index: n$_D^{25}$1.5308

$^1$H-NMR (CDCl$_3$, δ ppm) 1.26 (6H, d), 1.17-2.60 (8H, m), 2.60-3.20 (2H, m), 4.30-4.76 (1H, m), 4.56 (2H, d), 5.00-5.46 (2H, m), 5.50-6.30 (1H, m), 7.07 (1H, d, J =10), 8.05 (1H, d, J=7)

EXAMPLE 9

Preparation of Compound No. 7 (Table 2)

Substantially the same procedure as in Example 6 was repeated except that 2-chlorocarbonyl-1-cyclohexane carboxylic acid propargyl ester was used as the acid halide and 4-chloro-2-fluoro-5-isopropoxyaniline was used as the aniline derivative to obtain the Compound No. 7.

m.p.: 47° C.-48° C.

$^1$H-NMR (CDCl$_3$, δ ppm) 1.30 (6H, d), 1.13-2.50 (8H, m), 2.34 (1H, t), 2.60-3.25 (2H, m), 4.17-4.67 (1H, m), 4.67 (2H, d), 7.07 (1H, d, J=10), 7.56 (1H, br), 8.05 (1H, d, J =7)

EXAMPLE 10

Preparation of Compound No. 8 (Table 2)

Substantially the same operation as in Example 6 was repeated except that 2-chlorocarbonyl-1-cyclohexane carboxylic acid allyl ester was used as the acid halide to obtain the Compound No. 8.

Refractive Index: n$_D^{25}$1.5361

$^1$H-NMR (CDCl$_3$, δ ppm) 1.26 (8H, m), 2.56-3.17 (2H, m), 4.53 (4H, d), 4.94-5.46 (4H, m), 5.50-6.43 (2H, m), 7.03 (1H, d, J =10), 7.63 (1H, br), 8.63 (1H, d, J =7)

EXAMPLE 11

Preparation of Compound No. 9 (Table 2)

Substantially the same operation as in Example 6 was repeated except that 2-chlorocarbonyl-1-cyclohexane carboxylic acid allyl ester was used as the acid halide and 4-chloro-2-fluoro-5-propargyloxyaniline was used as the aniline derivative to obtain the Compound No. 9.

m.p.: 94° C.-96° C.

$^1$H-NMR (CDCl$_3$, δ ppm) 1.34-2.43 (8H, m), 2.50 (H, t), 2.59-3.26 (2H, m), 4.56 (2H, d), 4.73 (2H, d), 4.96-5.53 (2H, m), 5.56-6.26 (1H, m), 7.10 (1H, d, J =10), 7.67 (1H, br), 8.16 (1H, d, J =7)

EXAMPLE 12

Preparation of Compound No. 10 (Table 2)

Substantially the same operation as in Example 6 was repeated except that 2-chlorocarbonyl-1-cyclohexane carboxylic acid propargyl ester was used as the acid halide to obtain the Compound No. 10.

Refractive Index: n$_D^{25}$1 5470

$^1$H-NMR (CDCl$_3$, δ ppm) 1.26-2.59 (8H, m), 2.36 (1H, t), 2.63-3.17 (2H, m), 4.56 (2H, d), 4.67 (2H, d), 5.07-5.67 (2H, m), 7.03 (1H, d, J =10), 7.59 (1H, br), 8.00 (1H, d, J =7)

EXAMPLE 13

Preparation of Compound No. 11 (Table 2)

Substantially the same operation as in Example 6 was repeated except that 2-chlorocarbonyl-1-cyclohexane carboxylic acid propargyl ester was used as the acid halide and 4-chloro-2-fluoro-5-propargyloxyaniline was used as the aniline derivative to obtain the Compound No. 11.

m.p.: 89° C.-90° C.

$^1$H-NMR (CDCl$_3$, δ ppm) 1.33-2.33 (8H, m), 2.40 (1H, t), 2.56 (1H, t), 2.67-3.33 (2H, m), 4.69 (2H, d), 4.79 (2H, d), 7.48 (1H, d, J =10), 7.67 (1H, br), 8.13 (1H, d, J =7)

EXAMPLE 14

Preparation of Compound No. 12 (Table 2)

Substantially the same operation as in Example 6 was repeated except that 2-chlorocarbonyl-1-cyclohexane carboxylic acid allyl ester was used as the acid halide and 4-chloro-2-fluoro-5-(1-methyl-propynyloxy)aniline was used as the aniline derivative to obtain the Compound No. 12.

m.p.: 91° C.-93° C.

$^1$H-NMR (CDCl$_3$, δ ppm) 1.20-2.60 (12H, m), 2.61-3.22 (2H, m), 4.46-6.32 (6H, m), 7.10 (1H, d, J =10), 7.68 (1H, br), 8.18 (1H, d, J =7)

EXAMPLE 15

Preparation of Compound No. 13 (Table 2)

Substantially the same operation as in Example 6 was repeated except that 2-chlorocarbonyl-1-cyclohexane carboxylic acid propargyl ester was used as the acid halide and 4-chloro-2-fluoro-5-(1-methyl-propenyloxy)aniline was used as the aniline derivative to obtain the Compound No. 13.

Refractive Index: n$_D^{25}$1.5378

$^1$H-NMR (CDCl$_3$, δ ppm) 1.15-2.55 (12H, m), 2.58-3.20 (2H, m), 4.50-6.32 (6H, m), 7.00 (1H, d, J =10), 7.50 (1H, br), 8.00 (1H, d, J =7)

EXAMPLE 16

Test for Evaluation of Effectiveness in Growth Inhibition by Foliage Treatment

The same procedure as in Example 5 was repeated except that the compounds tested were Compound Nos. 4–13. Further, for comparison, the Comparative Compound A described in Example 4 was also tested. The results are shown in Table 6 below.

EXAMPLE 18

Preparation of N-(4-chloro-2-fluoro-5-isopropoxyphenyl)-2-(2-methoxy ethyloxycarbonyl)cyclohexyl carboxylic amide (Compound No. 14 (Table 3))

In 20 ml of methylene chloride, 0.69 g of 1,2,3,4,5,6-hexahydrophthalic acid 2-methoxyethyl monoester was dissolved. To this solution, 0.24 ml of pyridine and 0.22

TABLE 6

| Compound No. | Rate (a.i. g/10a) | Herbicidal Effectiveness | | | | | Phytotoxicity | | |
|---|---|---|---|---|---|---|---|---|---|
| | | Barnyard-grass | Pale smartweed | Slender amaranth | Cocklebur | Velvetleaf | Wheat | Corn | Soybean |
| 4 | 60 | 0 | 2 | 5 | 2 | 5 | 0 | — | 0 |
| | 125 | 2 | 2 | 5 | 2 | 5 | 0 | — | 1 |
| 5 | 30 | 0 | 1 | 5 | 0 | 5 | 0 | — | 0 |
| | 60 | 0 | 1 | 5 | 0 | 5 | 0 | — | 0 |
| 6 | 60 | 0 | 1 | 5 | 1 | 5 | 0 | — | 0 |
| | 125 | 0 | 4 | 5 | 3 | 5 | 0 | — | 1 |
| 7 | 60 | 0 | 2 | 4 | 2 | 5 | 0 | 0 | 2 |
| | 125 | 0 | 3 | 4 | 5 | 5 | 0 | 0 | 2 |
| 8 | 60 | 0 | 4 | 3 | 3 | 5 | 0 | 0 | 0 |
| | 125 | 2 | 5 | 4 | 5 | 5 | 0 | 0 | 0 |
| 9 | 30 | 3 | 5 | 5 | 4 | 5 | 0 | 0 | 0 |
| | 60 | 3 | 5 | 5 | 5 | 5 | 0 | 0 | 0 |
| 10 | 30 | 0 | 4 | 5 | 3 | 5 | 0 | 0 | 0 |
| | 60 | 1 | 5 | 5 | 3 | 5 | 0 | 0 | 0 |
| 11 | 30 | 3 | — | 5 | 3 | 5 | 0 | 0 | 0 |
| | 60 | 4 | — | 5 | 4 | 5 | 0 | 0 | 0 |
| 12 | 30 | 3 | 5 | 5 | 5 | 5 | 0 | 0 | 2 |
| | 60 | 4 | 5 | 5 | 5 | 5 | 0 | 0 | 2 |
| 13 | 30 | 3 | 5 | 5 | 5 | 5 | 0 | 0 | 2 |
| | 60 | 4 | 5 | 5 | 5 | 5 | 0 | 0 | 2 |
| Comparative Compound A | 30 | 0 | 2 | 3 | 3 | 3 | 1 | 0 | 5 |
| | 60 | 1 | 3 | 4 | 3 | 4 | 2 | 0 | 5 |

EXAMPLE 17

Test for Evaluation of Effectiveness in Growth Inhibition by Soil Treatment

The same procedure as in Example 4 was repeated except that the compounds tested were Compound Nos. 4–13. For comparison, the Comparative Compound A described in Example 4 was also tested. The results are shown in Table 7 below.

ml of thionyl chloride were added and the resulting mixture was stirred at room temperature. One hour later, 0.57 g of 4-chloro-2-fluoro-5-isopropoxyaniline and 0.42 ml of triethylamine were added to the mixture and the mixture was stirred at room temperature for 1.5 hours. After completion of the reaction, 10% hydrochloric acid was added to the reaction mixture to make the same acidic, and the mixture was extracted twice with methylene chloride. The extract was washed with saturated aqueous sodium hydrogen carbonate solution

TABLE 7

| Compound No. | Rate (a.i. g/10a) | Herbicidal Effectives | | | | | Phytoxicity Rice |
|---|---|---|---|---|---|---|---|
| | | Barnyard-grass | Small flower umbrellaplant | Bulrush | Monochoria | Annual broadleaved weeds | |
| 4 | 15 | 4 | 5 | 2 | 5 | 5 | 0 |
| | 30 | 5 | 5 | 2 | 5 | 5 | 0 |
| 5 | 15 | 5 | 5 | 3 | 5 | 5 | 0 |
| | 30 | 5 | 5 | 5 | 5 | 5 | 0 |
| 6 | 30 | 4 | 5 | 4 | 5 | 5 | 0 |
| | 60 | 4 | 5 | 4 | 5 | 5 | 0 |
| 7 | 15 | 4 | 5 | 3 | 5 | 5 | 0 |
| | 30 | 4 | 5 | 3 | 5 | 5 | 0 |
| 8 | 30 | 4 | 5 | 3 | 5 | 5 | 0 |
| | 60 | 4 | 5 | 5 | 5 | 5 | 0 |
| 9 | 15 | 5 | 5 | 2 | 5 | 5 | 0 |
| | 30 | 5 | 5 | 4 | 5 | 5 | 0 |
| 10 | 30 | 4 | 5 | 3 | 5 | 5 | 0 |
| | 60 | 5 | 5 | 3 | 5 | 5 | 0 |
| 11 | 30 | 5 | 5 | 3 | 5 | 5 | 0 |
| | 60 | 5 | 5 | 4 | 5 | 5 | 0 |
| 12 | 15 | 5 | 5 | 3 | 5 | 5 | 0 |
| | 30 | 5 | 5 | 4 | 5 | 5 | 0 |
| 13 | 15 | 4 | 5 | 2 | 5 | 5 | 0 |
| | 30 | 5 | 5 | 3 | 5 | 5 | 0 |
| Comparative Compound D | 30 | 3 | 5 | 3 | 5 | 5 | 2 |
| | 60 | 4 | 5 | 4 | 5 | 5 | 3 | and was dried over anhydrous magnesium sulfate. The solvent was evaporated under reduced pressure and the residue was purified by column chromatography (silica gel, hexane/ethyl acetate =3/1 (v/v)) to obtain 0.59 g of solid.

m.p.: 58° C.-60° C.

| | Element Analysis | | |
|---|---|---|---|
| | C | H | N |
| Found (%) | 57.47 | 6.42 | 3.36 |
| Calcd. (%) | 57.76 | 6.54 | 3.36 |

NMR (CDCl$_3$, δ ppm) 1.15-2.25 (14H, m), 2.60-3.16 (2H, m), 3.27 (3H, s), 3 30-3.70 (2H, m), 4.15-4.70 (3H, m), 7.05 (1H, d, J =10 Hz), 7.67 (1H, br), 8.16 (d, 1H, J =7 Hz)

EXAMPLE 19

Preparation of Compound No. 15 (Table 3)

Substantially the same procedure as in Example 18 was repeated except that 5-allylthio-4-chloro-2-fluoroaniline was used as the aniline derivative to obtain the Compound No. 15.

Refractive Index: $n_D$1.5587

| | Element Analysis | | |
|---|---|---|---|
| | C | H | N |
| Found (%) | 56.08 | 5.7 | 2.92 |
| Calcd. (%) | 55.87 | 5.86 | 3.25 |

NMR (CDCl$_3$, δ ppm) 1.15-2.62 (8H, m), 2.65-3.17 (2H, m), 3.30 (3H, s), 3.40-3.65 (4H, m), 4.15-4.38 (2H, m), 4.95-6.20 (3H, m), 7.09 (1H, d, J =10), 7.67 (1H, br), 8.35 (1H, d, J =8)

EXAMPLE 20

Preparation of Compound No. 16 (Table 3)

Substantially the same procedure as in Example 18 was repeated except that 4-chloro-2-fluoro-5-propargyloxyaniline was used as the aniline derivative to obtain the Compound No. 16.

m.p.: 92° C.-93° C.

| | Element Analysis | | |
|---|---|---|---|
| | C | H | N |
| Found (%) | 57.95 | 5.71 | 3.66 |
| Calcd. (%) | 58.32 | 5.62 | 3.4 |

NMR (CDCl$_3$, δ ppm) 1.15-2.42 (8H, m), 2.56 (1H, t, J =2), 2.65-3.15 (2H, m), 3.30 (3H, s), 3.35-3.65 (2H, m), 4.06-4.38 (2H, m), 4.72 (2H, d, J =2), 7.12 (1H, d, J =10), 7.76 (1H, br), 8.12 (1H, d, J =7)

EXAMPLE 21

Preparation of Compound No. 17 (Table 3)

Substantially the same procedure as in Example 18 was repeated except that 4-chloro-2-fluoro-5-(1-methylpropynyloxy)aniline was used as the aniline derivative to obtain the Compound No. 17.

m.p.: 68° C.-70° C.

| | Element Analysis | | |
|---|---|---|---|
| | C | H | N |
| Found (%) | 59.45 | 5.72 | 3.5 |
| Calcd. (%) | 59.22 | 5.91 | 3.28 |

NMR (CDCl$_3$, δ ppm) 1.15-2.40 (11H, m), 2.50 (1H, d, J =2), 2.60-3.20 (2H, m), 3.25 (3H, s), 3.40-3.65 (2H, m), 4.10-4.35 (2H, m), 4.90 (1H, dq, J =2.6), 7.08 (1H, d, J =10), 7.65 (1H, br), 8.20 (1H, m)

EXAMPLE 22

Preparation of Compound No. 18 (Table 3)

Substantially the same procedure as in Example 18 was repeated except that 4-chloro-2-fluoro-5-(1-methyl-3-butynyloxy)aniline was used as the aniline derivative to obtain the Compound No. 18.

Refractive Index: $n_D^{25}$1.5330

| | Element Analysis | | |
|---|---|---|---|
| | C | H | N |
| Found (%) | 60.22 | 6.07 | 2.79 |
| Calcd. (%) | 60.06 | 6.18 | 3.18 |

NMR (CDCl$_3$, δ ppm) 1.15-3.15 (16H, m), 3.28 (3H, s), 3.32-3.62 (2H, m), 4.00-4.65 (3H, m), 7.02 (1H, d, J =10), 7.60 (1H, br), 8.02 (1H, d, J =7)

EXAMPLE 23

Preparation of Compound No. 19 (Table 3)

Substantially the same procedure as in Example 18 was repeated except that 4-chloro-2-fluoro-5-(4-methoxy-2-butynyloxy)aniline was used as the aniline derivative to obtain the Compound No. 19.

Refractive Index: $n_D^{25}$1.5339

| | Element Analysis | | |
|---|---|---|---|
| | C | H | N |
| Found (%) | 57.78 | 5.81 | 3.01 |
| Calcd. (%) | 57.95 | 5.96 | 3.07 |

NMR (CDCl$_3$, δ ppm) 1.15-2.50 (8H, m), 2.55-3.08 (2H, m), 3.15-3.68 (8H, m), 3.95-4.30 (4H, m), 4.72 (2H, t, J =1), 7.02 (1H, d, J =10), 7.65 (1H, br), 8.12 (1H, d, J =7)

EXAMPLE 24

Preparation of Compound No. 20 (Table 3)

Substantially the same procedure as in Example 18 was repeated except that 4-chloro-2-fluoro-5-propargylthioaniline was used as the aniline derivative to obtain the Compound No. 20.

Refractive Index: $n_D^{25}$1.5612

| | Element Analysis | | |
|---|---|---|---|
| | C | H | N |
| Found (%) | 56.16 | 5.30 | 2.97 |
| Calcd. (%) | 56.13 | 5.41 | 3.27 |

NMR (CDCl$_3$, δ ppm) 1.20-2.60 (9H, m), 2.70-3.25 (2H, m), 3.32 (3H, s), 3.34-3.80 (4H, m), 4.10-4.45 (2H, m), 7.20 (1H, d, J =10), 7.83 (1H, br), 8.48 (1H, d, J =7)

EXAMPLE 25

Preparation of Compound No. 21 (Table 3)

Substantially the same procedure as in Example 18 was repeated except that 2,4-dichloro-5-(1-methylpropynyloxy)aniline was used as the aniline derivative to obtain the Compound No. 21.

Refractive Index: $n_D^{25}$ 1.5437

| | Element Analysis | | |
|---|---|---|---|
| | C | H | N |
| Found (%) | 56.81 | 5.67 | 3.17 |
| Calcd. (%) | 57.02 | 5.69 | 3.16 |

NMR (CDCl$_3$, δ ppm) 1.15–2.37 (11H, m), 2.50 (1H, d, J =2), 2.60–3.13 (2H, m), 3.24 (3H, s), 3.30–3.63 (2H, m), 4.05–4.32 (2H, m), 4.90 (1H, dq, J =1, 7), 7.25 (1H, s), 7.85 (1H, br), 8.28 (1H, d, J =2)

EXAMPLE 26

Preparation of Compound No. 22 (Table 3)

Substantially the same procedure as in Example 21 was repeated except that 2-chlorocarbonyl-1-cyclohexane carboxylic acid 2-tetrahydrofuranylmethyl ester was used as the acid halide to obtain the Compound No. 22.

m.p.: 101° C.–102° C.

| | Element Analysis | | |
|---|---|---|---|
| | C | H | N |
| Found (%) | 60.88 | 6.13 | 3.22 |
| Calcd. (%) | 61.12 | 6.02 | 3.09 |

NMR (CDCl$_3$, δ ppm) 1.15–2.35 (15H, m), 2.50 (1H, d, J =2), 2.57–3.20 (2H, m), 3.50–4.35 (5H, m), 4.85 (1H, dq, J =2,6), 7.12 (1H, d, J =10), 7.73 (1H, br), 8.20 (1H, dd, J =2,

EXAMPLE 27

Preparation of Compound No. 23 (Table 3)

Substantially the same procedure as in Example 18 was repeated except that 4-chloro-2-fluoro-5-(1-cyanoethoxy)aniline was used as the aniline derivative to obtain the Compound No. 23.

m.p.: 79° C.–82° C.

| | Element Analysis | | |
|---|---|---|---|
| | C | H | N |
| Found (%) | 55.93 | 5.53 | 6.52 |
| Calcd. (%) | 56.27 | 5.66 | 6.56 |

NMR (CDCl$_3$, δ ppm) 1.20–2.50 (11H, m), 2.60–3.10 (2H, m), 3.15–3.70 (5H, m), 4.08–4.38 (2H, m), 4.92 (1H, q, J =7 ), 7.12 (1H, d, J =10), 7.74 (1H, br), 8.24 (1H, d, J =7)

EXAMPLE 28

Preparation of Compound No. 24 (Table 3)

Substantially the same procedure as in Example 18 was repeated except that 4-chloro-2-fluoro-5-[1-(3-methyl-1,2,4-oxadiazol-5-yl) ethoxy)aniline was used as the aniline derivative to obtain the Compound No. 24.

Refractive Index: $n_D^{25}$ 1.5300

| | Element Analysis | | |
|---|---|---|---|
| | C | H | N |
| Found (%) | 54.83 | 5.59 | 8.79 |
| Calcd. (%) | 54.60 | 5.62 | 8.68 |

NMR (CDCl$_3$, δ ppm) 1.20–2.20 (11H, m), 2.35 (3H, s), 2.65–3.10 (2H, m), 3.25 (3H, s), 3.30–3.60 (2H, m), 4.30–4.40 (2H, m), 5.45 (1H, q, J =7), 7.03 (1H, d, J =120), 7.58 (1H, br), 8.06 (1H, d, J =7)

EXAMPLE 29

Preparation of Compound No. 25

Substantially the same procedure as in Example 18 was repeated except that 4-chloro-2-fluoro-5-[1-(4-methoxybenzenesulfonylamiono carbonyl)ethoxy)aniline was used as the aniline derivative to obtain the Compound No. 25 (viscose substance).

| | Element Analysis | | |
|---|---|---|---|
| | C | H | N |
| Found (%) | 52.55 | 5.42 | 4.6 |
| Calcd. (%) | 52.72 | 5.24 | 4.55 |

NMR (CDCl$_3$, δ ppm) 1.05–2.50 (11H, m), 2.58–3.12 (2H, m), 3.28 (3H, s), 3.40–3.68 (2H, m), 3.82 (3H, s), 4.10–4.40 (2H, m), 4.67 (1H, q, J =7), 6.80–7.20 (4H, m), 7.60–8.15 (4H, m)

EXAMPLE 30

Test for Evaluation of Effectiveness in Growth Inhibition by Soil Treatment

The same procedure as in Example 4 was repeated except that the compounds tested were Compound Nos. 14–25. For comparison, the Comparative Compound A described in Example 4 was also tested. The results are shown in Table 8 below.

TABLE 8

| Compound No. | Rate (a.i. g/10a) | Rice | Barnyardgrass | Small flower umbrellaplant | Monochoria | Annual broadleaved weeds |
|---|---|---|---|---|---|---|
| 14 | 60 | 0 | 5 | 5 | 5 | 5 |
|  | 30 | 0 | 4 | 5 | 5 | 5 |
| 15 | 60 | 0 | 5 | 5 | 5 | 5 |
|  | 30 | 1 | 5 | 5 | 5 | 5 |
| 16 | 60 | 0 | 5 | 5 | 5 | 5 |
|  | 30 | 0 | 4 | 5 | 5 | 5 |
| 17 | 60 | 0 | 5 | 5 | 5 | 5 |
|  | 30 | 0 | 4 | 5 | 5 | 5 |
| 18 | 60 | 0 | 5 | 5 | 5 | 5 |
|  | 30 | 0 | 4 | 5 | 5 | 5 |

TABLE 8-continued

| Compound No. | Rate (a.i. g/10a) | Rice | Barnyard-grass | Small flower umbrellaplant | Monochoria | Annual broadleaved weeds |
|---|---|---|---|---|---|---|
| 19 | 60 | 0 | 5 | 5 | 5 | 5 |
|  | 30 | 0 | 4 | 5 | 5 | 5 |
| 20 | 60 | 0 | 5 | 5 | 5 | 5 |
|  | 30 | 0 | 4 | 5 | 5 | 5 |
| 21 | 60 | 0 | 5 | 5 | 5 | 5 |
|  | 30 | 0 | 4 | 5 | 5 | 5 |
| 22 | 60 | 0 | 5 | 5 | 5 | 5 |
|  | 30 | 0 | 4 | 5 | 5 | 5 |
| 23 | 60 | 0 | .5 | 5 | 5 | 5 |
|  | 30 | 0 | 4 | 5 | 5 | 5 |
| 24 | 60 | 0 | 5 | 5 | 5 | 5 |
|  | 30 | 0 | 4 | 5 | 5 | 5 |
| 25 | 60 | 0 | 5 | 5 | 5 | 5 |
|  | 30 | 0 | 4 | 5 | 5 | 5 |
| Comparative Compound A | 60 | 3 | 4 | 5 | 5 | 5 |
|  | 30 | 2 | 3 | 5 | 4 | 5 |

EXAMPLE 31

Test for Evaluation of Effectiveness in Growth Inhibition by Foliage Treatment

The same procedure as in Example 5 was repeated except that the compounds tested were Compound Nos. 14–25. Further, for comparison, the Comparative Compound A described in Example 4 was also tested. The results are shown in Table 9 below.

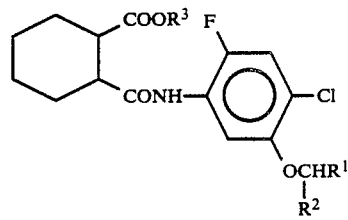

TABLE 9

| Compound No. | Rate (a.i. g/10a) | Herbicidal Effectiveness ||||| Phytotoxicity |||
|---|---|---|---|---|---|---|---|---|---|
|  |  | Barnyard-grass | Pale smartweed | Slender amaranth | Cocklebur | Velvetleaf | Wheat | Corn | Soybean |
| 14 | 60 | 5 | 5 | 5 | 5 | 5 | 0 | 0 | 2 |
|  | 30 | 4 | 5 | 5 | 4.5 | 5 | 0 | 0 | 2 |
| 15 | 60 | 5 | 5 | 5 | 5 | 5 | 0 | 0 | 2 |
|  | 30 | 5 | 5 | 5 | 5 | 5 | 0 | 0 | 1 |
| 16 | 60 | 5 | 5 | 5 | 5 | 5 | 0 | 0 | 2 |
|  | 30 | 5 | 5 | 5 | 5 | 5 | 0 | 0 | 2 |
| 17 | 60 | 5 | 5 | 5 | 5 | 5 | 1 | 0 | 2 |
|  | 30 | 4 | 5 | 5 | 5 | 5 | 1 | 0 | 2 |
| 18 | 60 | 0 | 5 | 5 | 5 | 5 | 0 | 0 | 1 |
|  | 30 | 0 | 3 | 5 | 5 | 5 | 0 | 0 | 1 |
| 19 | 60 | 4 | 4 | 5 | 5 | 5 | 0 | 0 | 1 |
|  | 30 | 3 | 2 | 4 | 5 | 5 | 0 | 0 | 1 |
| 20 | 60 | 5 | 4 | 5 | 5 | 5 | 0 | 0 | 2 |
|  | 30 | 5 | 4 | 5 | 5 | 5 | 0 | 0 | 1 |
| 21 | 60 | 4 | 5 | 5 | 5 | 5 | 0 | 0 | 2 |
|  | 30 | 4 | 5 | 5 | 5 | 5 | 0 | 0 | 2 |
| 22 | 60 | 3 | 5 | 5 | 5 | 5 | 1 | 0 | 2 |
|  | 30 | 3 | 5 | 4 | 5 | 5 | 0 | 0 | 1 |
| 23 | 60 | 4 | 5 | 5 | 5 | 5 | 0 | 0 | 2 |
|  | 30 | 4 | 5 | 5 | 5 | 5 | 0 | 1 | 2 |
| 24 | 60 | 4 | 5 | 5 | 4 | 5 | 0 | 0 | 0 |
|  | 30 | 4 | 4 | 5 | 3 | 5 | 0 | 0 | 0 |
| 25 | 60 | 0 | 0 | 5 | 4 | 5 | 0 | 0 | 0 |
|  | 30 | 0 | 0 | 5 | 3 | 5 | 0 | 0 | 0 |
| Comparative Compound A | 60 | 1 | 3 | 3 | 3 | 4 | 2 | 0 | 5 |
|  | 30 | 0 | 2 | 2 | 3 | 3 | 1 | 0 | 5 |

We claim:

1. A hexahydrophthalic anilide derivative of the formula [I]:

wherein $R^1$ represents non-substituted or substituted phenyl, $R^2$ represents hydrogen or $C_1$–$C_4$ alkyl, $R^3$ represents $C_1$–$C_4$ alkyl or $C_1$–$C_4$ alkenyl.

2. The hexahydrophthalic anilide derivative of claim 1, wherein $R^1$ represents phenyl.

3. A hexahydrophthalic anilide derivative of the formula [II]:

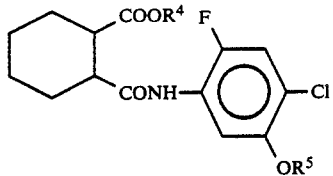

wherein $R^4$ and $R^5$, the same or different, represent $C_1$–$C_4$ alkyl, $C_1$–$C_4$ alkenyl or $C_1$–$C_4$ alkynyl, provided $R^4$ and $R^5$ are not $C_1$–$C_4$ alkyl simultaneously.

4. A hexahydrophthalic anilide derivative of the formula:

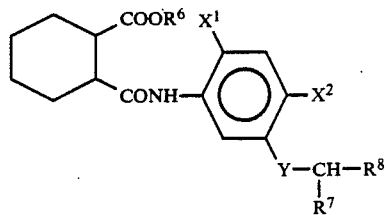

wherein $X^1$ and $X^2$, the same or different, represent halogen Y, represents oxygen or sulfur, $R^6$ represents $C_1$–$C_6$ straight alkyl group which is substituted with a $C_1$–$C_3$ alkoxy group, tetrahydrofurfuryl or 2-perhydropyranylmethyl, $R^7$ represents hydrogen or methyl, $R^8$ represents cyano, $C_1$–$C_3$ alkyl, $C_2$ or $C_3$ alkenyl, $C_2$–$C_4$ alkynyl, $C_3$–$C_6$ alkynyl which is substituted with methoxy, $CONHR^9$, wherein $R^9$ represents aromatic sulfonyl, or an azole heterocyclic ring.

5. The hexahydrophthalic anilide derivative of claim 4, wherein $X^1$ and $X^2$, the same or different, represent fluorine or chlorine.

6. The hexahydrophthalic anilide derivative of claim 5, wherein $R^6$ represents methoxyethyl or tetrahydrofurfuryl.

7. The hexahydrophthalic anilide derivative of claim 5, wherein $R^8$ represents 1,2,4-oxadiazolyl or which 3-position is substituted with $C_1$–$C_3$ alkyl.

8. The hexahydrophthalic anilide derivative of claim 5, wherein $R^9$ represents anisyl sulfonyl.

* * * * *